(12) United States Patent
Wiedenmann et al.

(10) Patent No.: US 6,350,357 B1
(45) Date of Patent: Feb. 26, 2002

(54) SENSOR ELEMENT

(75) Inventors: Hans-Martin Wiedenmann, Stuttgart; Harald Neumann, Vaihingen; Karl-Heinz Heussner, Leonberg, all of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/142,599

(22) PCT Filed: Nov. 29, 1997

(86) PCT No.: PCT/DE97/02792

§ 371 Date: Jun. 17, 1999

§ 102(e) Date: Jun. 17, 1999

(87) PCT Pub. No.: WO98/30894

PCT Pub. Date: Jul. 16, 1998

(30) Foreign Application Priority Data

Jan. 13, 1997 (DE) .......................... 197 00 700

(51) Int. Cl.⁷ ............................................ G01N 27/407
(52) U.S. Cl. ...................... 204/426; 204/408; 204/427; 204/429
(58) Field of Search .................. 204/421–429, 204/408

(56) References Cited

U.S. PATENT DOCUMENTS

| 4,294,679 A | | 10/1981 | Maurer et al. | |
|---|---|---|---|---|
| 4,334,974 A | * | 6/1982 | Muller et al. | 204/425 |
| 5,298,147 A | * | 3/1994 | Nakae et al. | 204/426 |
| 5,447,618 A | * | 9/1995 | Sugiyama et al. | 204/426 |
| 5,562,811 A | * | 10/1996 | Lenfers | 204/426 |
| 5,670,032 A | | 9/1997 | Friese et al. | |

FOREIGN PATENT DOCUMENTS

| DE | 29 07 032 | 8/1980 |
|---|---|---|
| DE | 43 42 731 | 2/1995 |
| JP | 03 158751 | 10/1991 |

* cited by examiner

Primary Examiner—T. Tung
(74) Attorney, Agent, or Firm—Kenyon & Kenyon

(57) ABSTRACT

A plate-shaped sensor element is proposed, in particular for determining the oxygen level in exhaust gases of internal combustion engines. The sensor element has at least one measuring cell with an oxygen-ion-conducting solid electrolyte and a heating element, the measuring cell and the heating element being connected with an electrical insulation layer. The material of the insulation layer is made of at least one crystalline, non-metallic material and at least one glass-forming material, a glazing filled with the crystalline, non-metallic material being formed when the sensor element is sintered.

8 Claims, 1 Drawing Sheet

SENSOR ELEMENT

BACKGROUND INFORMATION

German Patent Application No. 43 42 731 describes a gas sensor with a tubular finger-shapes sensor element in which one of the printed conductors running on the outside of the tubular sensor element is covered by an electrically insulating layer formed by a mixture of a crystalline, non-metallic material and a glass-forming material, a glazing, filled with the crystalline non-metallic material being formed upon heating.

Furthermore, German Patent Application No. 29 07 032 corresponding to U.S. Pat. No. 4,294,679), for example, describes a planar sensor .a element for determining the oxygen level in gases, in which a measuring cell is connected to a resistance heating element via an $Al_2O_3$ insulating layer. The ceramic heater insulation made of $Al_2O_3$ is electrically insulating and is used porously sintered to compensate for the different sinter contractions and different thermal expansion coefficients of $Al_2O_3$ and the adjacent $ZrO_2$ solid electrolyte layer. This, however, has the disadvantage that gaseous and liquid components diffuse from the exhaust gas into the reference atmosphere through the porous insulation layer and thus affect the measuring signal. In addition, components of the exhaust.

SUMMARY OF THE INVENTION

The gas sensor according to the present invention has the advantage that the insulation layer is gas-tight and has a good electrical insulation capability, good adhesion to the solid electrolyte ceramic, and good heat conductivity. The good adhesion results, in particular, from the fact that shrinkage of the insulation layer material due to sintering is approximately equal to that of the solid electrolyte ceramic material. The compression stresses arising in the insulation layer due to the different thermal expansion coefficients of the insulation layer and the solid electrolyte foil are reduced in part by the plastic deformation due to the softening characteristics of the glass phase and uniformly distributed over the boundary surface with the solid electrolyte ceramic. Thus local stress concentrations that might cause cracks are fully avoided. The glass materials used have an initial softening temperature that is lower than the 1250° C sintering temperature. The powder mixture used in the process for manufacturing the sensor element has proved to be particularly well-suited. The paste produced with the powder mixture is particularly well-suited for screen printing of the gas-tight insulation layers.

The particular the properties regarding gas-tightness and heat conductivity are achieved if $Al_2O_3$ with a particle size of $d_{50}<0.40$ μm is used as the crystalline, non-metallic material. Gas-tightness of the insulation layer is further improved when a particle size distribution of $d_{90}<1$ μm is set. With this particle size and particle size distribution, a gas tightness 2 to 4 times greater than is achievable with conventional ceramic layers can be achieved. $d_{50}$ denotes the average particle size referred to the mass; $d_{90}$ denotes the particle size with 90% of the mass being finer or the same. By suitable selection of particle size and particle size distribution of materials B and C in the following table, the sintering temperature can be reduced from 1600° C. to 1250° C. The melting point of the glass-forming material, with which a glazing filled with a crystalline, non-metallic material, for example, $Al_2O_3$, is formed, is the limit for the sintering temperature. An insulation layer that is particularly well-suited for heater insulation is achieved with a proportion of 60 wt. % of crystalline non-metallic material to 40 wt. % of glass-forming material in the raw material mixture.

DETAILED DESCRIPTION

Figure 1:
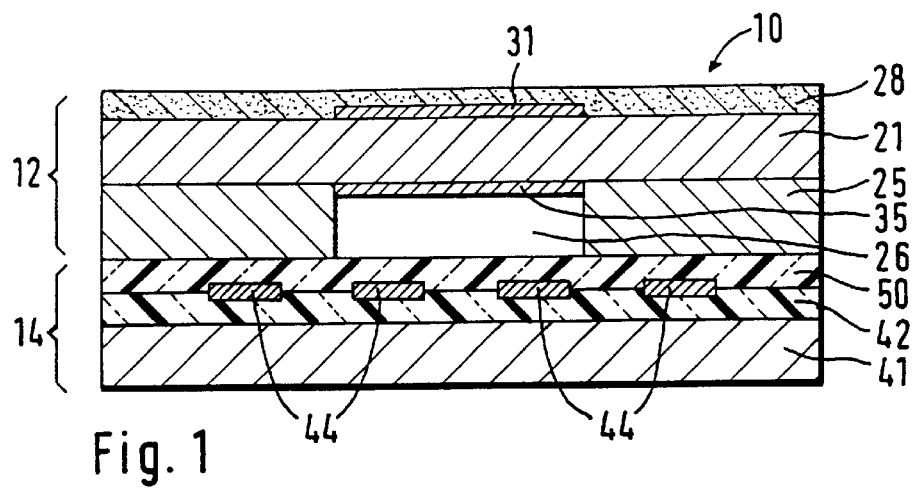
FIG. 1 shows a cross-section through an exhaust-gas-side part of a sensor element.
Figure 2:
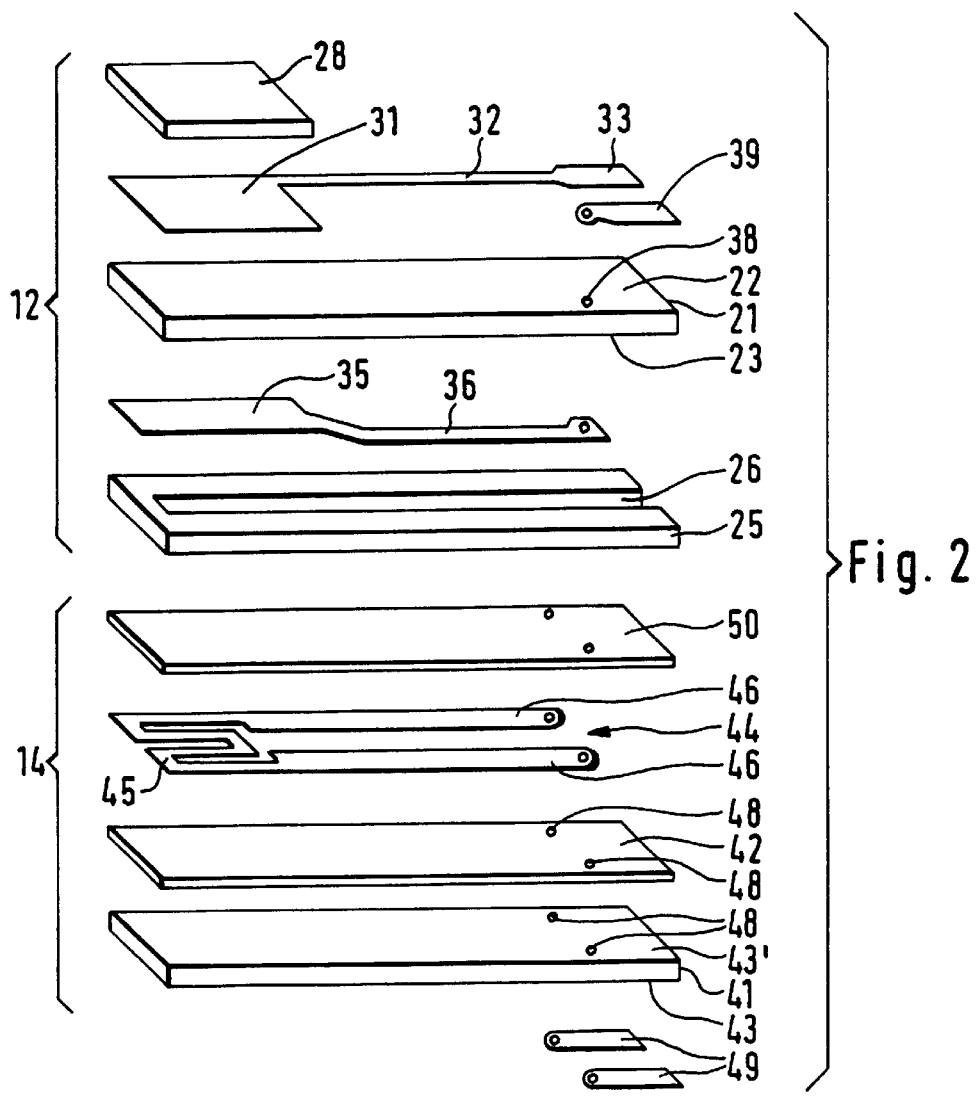
FIG. 2 shows an enlarged view of a layer system of the sensor element illustrated in FIG. 1.

Plate-shaped sensor element 10 illustrated in FIGS. 1 and 2 has an electrochemical measuring cell 12 and a heating element 14. Measuring cell 12 has, for example, a first solid electrolyte foil 21 with a large surface 22 on the measured gas side and a large surface 23 on the reference gas side, as well as a second solid electrolyte foil 25 with a reference channel 26 integrated therein. On large surface 22 on the measured gas side there is a measuring electrode 31 with a printed conductor 32 and a first terminal contact 33. On large surface 23 on the reference gas side of first solid electrolyte foil 21, there is a reference electrode 35 with a printed conductor 36. Furthermore, a through-plating 38 is provided in first solid electrolyte foil 21, through which printed conductor 36 of reference electrode 35 is guided to large surface 22 on the measured gas side. In addition first terminal contact 33, a second terminal contact 39, connected to through-plating 38 and thus forming the contact point for reference electrode 35, is also located on large surface 22. Measuring electrode 31 is covered with a porous protective layer 28.

Heating element 14 has, for example, a support foil 41 with an outer large surface 43 and an inner large surface 43', which, in this embodiment is composed of the material of the two solid electrolyte foils 21, 25. An outer insulation layer 42 is applied to inner large surface 43' of support foil 41. A resistance heater 44 with a wave-form heating conductor 45 and two terminal conductors 46 is located on outer insulation layer 42. Outer insulation layer 42 and support foil 41 have two heater through-platings 48 each flush to one another, which run from the two terminal conductors 46 to outer large surface 43 of support foil 41. Two heater terminal contacts 49 are arranged on outer large surface 43 of support foil 41, which are connected to heater through-platings 48.

An inner insulation layer 50 is on resistance heater 44. The large surface of inner insulation layer 50 is connected to the large surface of the second solid electrolyte foil 25. Thus heating element 14 is thermally connected to measuring cell 12 via inner insulation layer 50.

The two solid electrolyte foils 21 and 25 and support foil 41 are composed of $ZrO_2$, partially stabilized with 5 mol. % $Y_2O_3$, for example. Electrodes 31, 35, printed conductors 32, 36, through-platings 38 and terminal contacts 33, 39 are made of platinum cermet, for example. In this embodiment, a platinum cermet is also used as the material for the resistance heater, the ohmic resistance of leads 46 being selected to be less than that of heating conductor 45.

A screen printing paste with the following composition is used for producing insulating layers 42 and 50:

50 wt. % powder mixture 40 wt. % organic solvent 5 wt. % organic plasticizer 5 wt. % organic binder.

The composition may vary as follows:

Powder mixture: 20 to 70 wt. %

Solvent: 20 to 70 wt. %

Plasticizer: 1 to 15 wt. %

Binder: 1 to 15 wt. %.

Hexanol can be used as the solvent, for example, phthalate as the plasticizer and polyvinylbutyral as the binder, for example.

The raw material components are homogenized in appropriate mixing units such as ball mills or three-roller mills, so that a paste suitable for screen printing is obtained.

The powder mixture contains $Al_2O_3$ (alumina), for example with a specific sintering activity and a glass-forming material, such as an alkaline earth silicate glass. Ba—Al silicate can be used, for example, as an alkaline earth silicate glass. Barium can be replaced with strontium up to 30 atomic %.

The alkaline earth silicate glass can be introduced as a pre-melted glass frit or as a glass-phase raw material mixture. The material mixture may contain electrically conducting impurities up to 1 wt. %. This concerns, in particular, $Na_2O$, $K_2O$, $Fe_2O_3$, $TiO_2$, $Cu_2O$, or other semiconducting oxides. The level of electrically conducting impurities in commercially available raw materials is usually less than 0.2 wt. %.

Alumina is selected so that, at a sintering temperature needed for forming a glazing filled with alumina when the powder mixture is sintered, alumina alone has a sintering activity resulting in a relative sintering density of at least 95%. This is the case of aluminas B and C in the table below. The table shows the actual sintering density $\rho_S$ in g/cm$^3$ and the relative sintering density $\rho_S/\rho_{th}$ in % for three different aluminas A, B and C.

| Parameter | Alumina A | Alumina B | Alumina C |
|---|---|---|---|
| Particle Size: | | | |
| $d_{50}$ (μm) | 0.45 | 0.34 | 0.20–0.30 |
| $d_{90}$ (μm) | 1.6–2.6 | 0.50 | 0.30–0.40 |
| Sintering Activity | | | |
| $t_s$ (° C.) for $\rho_s$ = 3.80 g/cm$^3$ | 1490 | 1330 | 1280 |
| $\rho_s/\rho_{th}$ = 95% $\rho_s$ (g/cm$^3$) for $t_s$ = 1400° C. after 2 h in air $\rho_s/\rho_{th1}$ (%) | 3.43 85.7 | 3.90 97.5 | 3.96 99.0 |

In addition to aluminas B or C, also Mg spinel, fosterite or a mixture of these substances can be used as crystalline non-metallic materials. It is also possible to add Mg spinel, fosterite or a mixture of these substances to powder mixtures with aluminas B or C. These crystalline, non-metallic materials must, however, have a sintering activity that results in a sintering density of at least 95%.

EXAMPLE 1

Composition of the powder mixture:

60 wt. % Alumina B or C (see Table), 40 wt. % Ba—Al silicate glass powder (53 wt. % BaO, 5 wt. % $Al_2O_3$, 42 wt. % $SiO_2$, specific surface area 5 m$^2$/g), Insulation resistance<1 MΩ.

The powder mixture is homogenized and ground in a ball mill with 90% $Al_2O_3$ grinding balls. Then an aqueous slurry is added with 500 g raw material mixture made up of alumina and Ba—Al silicate glass, 500 ml distilled water and 25 ml 10% aqueous polyvinyl alcohol solution. The slurry is ground in a ball mill with 90% $Al_2O_3$ grinding balls for 1.5 hours.

EXAMPLE 2

This example differs from the powder mixture in Example 1 by the fact that instead of 40% wt. % Ba—Al silicate glass powder, the following composition is selected:

38 wt. % Ba—Al silicate glass powder, 1 wt. % kaolin, 1 wt. % barium carbonate ($BaCO_3$, chemically pure), Insulation resistance >1 MΩ.

EXAMPLE 3

The composition of the powder mixture differs from that of Example 1 by the fact that instead of the Ba—Al silicate glass powder the following components are used:

40 wt. % of a calcinate composed of:

11 wt. % kaolin, 34 wt. % quartz (99% $SiO_2$)

55 wt. % $BaCo_3$ (chemically pure).

The components are ground in a ball mill with 90% $Al_2O_3$ for two hours and calcined as loose particles in corundum capsules in an oxidizing atmosphere at 1000° C. for two hours and then ground again as described above.

Insulation resistance >1 MΩ.

EXAMPLE 4

The composition of the powder mixture differs from that of Example 1 and Example 3 in the following:

70 wt. % alumina and 30 wt. % calcinate,

Insulation resistance >1 MΩ.

EXAMPLE 5

As in Example 4, but instead of alumina with: 70 wt. % partially stabilized $ZrO_2$ with 3.5 wt. % MgO (35% monocline), Specific surface area: 7 m$^2$/g Insulation resistance >60 kΩ.

EXAMPLE 6

As Example 3, but:

50 wt. % alumina, 50 wt. % calcinate,

Insulation resistance >1 MΩ.

EXAMPLE 7

As Example 3, but:

85 wt. % alumina, 15 wt. % calcinate,

Insulation resistance >500 kΩ.

EXAMPLE 8

The composition corresponds to that of Example 7, with alumina containing the following components:

99.3% $Al_2O_3$, 0.3% $Na_2O$

Specific surface area: 2.5 $m_2/g$,

Insulation resistance >300 kΩ.

EXAMPLE 9

The composition corresponds to that of Example 3, but instead of alumina, with the following components:

60 wt. % Mg spinel powder ($MgO \cdot Al_2O_3$) with <0.5 wt. % free MgO and <0.1 wt. % $Na_2O$ Specific surface area: 8 $m^2/g$, Insulation resistance >1 MΩ.

For preparing the layer system for sensor element 10 shown in FIGS. 1 and 2, the prepared paste is initially applied to ceramic support foil 41 using screen printing. Thus resistance heater 44 is printed onto insulation layer 42 using screen printing and a conventional cermet paste. Through-platings 48, previously removed from insulation layer 42 and applied to support foil 41, are made at the same time. The inner insulation layer 50 is applied to resistance heater 44 also using screen printing techniques. The layer thicknesses of insulation layers 42, 50, which must be present prior to sintering, are set using an appropriate number of screen printing steps and/or by an appropriate selection of the screen printing parameters and paste properties (viscosity, etc.). In the exemplary embodiment, outer insulation layer 42 has a thickness of 18 μm and inner insulation layer 50 also has a thickness of 18 μm after sintering.

Heater element 41 thus manufactured is now laminated together with measuring cell 12, which is also manufactured using printing techniques, and co-sintered at approximately 1400° C. At the sintering temperature, the ceramic and metallic components of the layer system are sintered. Thus the gas-tight electrical insulation layers 42 and 50 are formed by fusing the glass-forming material and sintering the crystalline components.

What is claimed is:

1. A sensor element, comprising:

an electrical insulation layer;

at least one measuring cell; and at least one heating element connected to the at least one measuring cell via the electrical insulation layer, wherein the electrical insulation layer is composed of at least one crystalline non-metallic material and at least one glass-forming material to form a glazing filled with the at least one crystalline non-metallic material, and wherein the glazing is formed when the sensor element is sintered.

2. The sensor element according to claim 1, wherein the at least one crystalline non-metallic material includes one of $Al_2O_3$, Mg spine, forsterite, and a mixture of $Al_2O_3$, Mg spinel, and forsterite.

3. The sensor element according to claim 1, wherein the at least one glass-forming material includes an alkaline earth silicate glass.

4. The sensor element according to claim 3, wherein the alkaline earth silicate glass includes a barium-aluminum silicate glass.

5. The sensor element according to claim 4, wherein up to 30 atomic percent of barium in the barium-aluminum silicate glass is replaced with strontium.

6. The sensor element according to claim 1, wherein the at least one measuring cell includes a solid electrolyte body composed of partially stabilized $ZrO_2$.

7. The sensor element according to claim 1, wherein the at least one crystalline non-metallic material constitutes at least 50% by weight of solid material components of the insulation layer.

8. The sensor element according to claim 1, wherein the sensor element is configured to determine an oxygen level in an exhaust gas of an internal combustion engine.

* * * * *

UNITED STATES PATENT AND TRADEMARK OFFICE
CERTIFICATE OF CORRECTION

PATENT NO. : 6,350,357 B1
DATED : February 26, 2002
INVENTOR(S) : Wiedenmann et al.

It is certified that error appears in the above-identified patent and that said Letters Patent is hereby corrected as shown below:

Column 1,
Line 15, delete ".a".
Line 26, change "exhaust" to -- exhaust gas may deposit on the resistance heater and damage it --.
Line 50, delete "particular the".

Signed and Sealed this

Twenty-fourth Day of June, 2003

JAMES E. ROGAN
*Director of the United States Patent and Trademark Office*